United States Patent [19]

Ernst

[11] Patent Number: 4,499,291

[45] Date of Patent: Feb. 12, 1985

[54] PROCESS FOR SIMULTANEOUS HYDROGENATION OF 2-BUTYNE-1,4-DIOL AND FURAN

[75] Inventor: Richard E. Ernst, Kennett Square, Pa.

[73] Assignee: E. I. Du Pont de Nemours and Company, Wilmington, Del.

[21] Appl. No.: 517,589

[22] Filed: Jul. 27, 1983

[51] Int. Cl.³ .......................................... C07D 307/08
[52] U.S. Cl. .................................................. 549/429
[58] Field of Search ........................................ 549/429

[56] References Cited

U.S. PATENT DOCUMENTS

| 2,033,292 | 3/1936 | Lazier | 549/429 |
| 2,319,707 | 5/1943 | Reppe et al. | 549/429 |
| 2,335,795 | 11/1943 | Reppe et al. | 549/429 |

FOREIGN PATENT DOCUMENTS 1242358  8/1971  United Kingdom ............... 568/861

Primary Examiner—Robert T. Bond

[57] ABSTRACT

The hydrogenation of furan to tetrahydrofuran can be carried out simultaneously with the hydrogenation of 2-butyne-1,4-diol to 1,4-butanediol. This can be done in the same reactor, using a common catalyst, and under common reaction conditions.

4 Claims, No Drawings

PROCESS FOR SIMULTANEOUS HYDROGENATION OF 2-BUTYNE-1,4-DIOL AND FURAN

TECHNICAL FIELD

This invention relates to a process for the catalytic hydrogenation of 2-butyne-1,4-diol (butynediol) to 1,4-butanediol, and to a process for the catalytic hydrogenation of furan to tetrahydrofuran (THF). It is more particularly directed to a method whereby these hydrogenations can be performed simultaneously.

BACKGROUND AND SUMMARY OF THE INVENTION

The catalytic hydrogenation of butynediol to butanediol is well known, and is described, for example, in British Pat. No. 1,242,358. In that British process, an aqueous solution of butynediol is catalytically hydrogenated at a temperature of 60°–150° C., under hydrogen pressure, using Raney nickel as the catalyst.

The process of catalytically hydrogenating furan to THF is also known.

It has now been found, according to the invention, that the catalytic hydrogenation of furan to THF can be carried out simultaneously with the catalytic hydrogenation of butynediol to butanediol. This can be done in the same reaction vessel, using a common catalyst, under the same conditions as the butynediol-butanediol hydrogenation, and can provide great savings in time, effort and money.

DETAILED DESCRIPTION OF THE INVENTION

The process of the invention can be run as described in British Pat. No. 1,242,358, the disclosures of which are incorporated into this specification to show procedures, reaction conditions, and to describe the nature of the catalyst and how it is prepared.

Briefly, in the British process, an aqueous solution of butynediol, ordinarily a 20–70% by weight solution, is passed through a reactor packed with a Raney nickel catalyst. This catalyst is a granular foraminous alloy of 40–45% by weight of nickel and 55–60% by weight of aluminum, which has been activated by removal of 5–100% of its aluminum by leaching with alkali. Although Raney nickel is the catalyst of choice, it should be understood that other conventional hydrogenation catalysts, such as platinum, palladium and supported or promoted nickel, can also be used.

Hydrogenation in the British process is ordinarily conducted at a pH of 6.5–11, preferably 7–8, a temperature of 60°–150° C., preferably 70°–145° C., and under a partial hydrogen pressure of 17236–37920 kPa (2500–5500 psi), with a superficial gas velocity of at least 15.25 cm (0.5 foot) per minute.

The process of the invention is ordinarily and preferably run continuously, although it can also be run batchwise if desired.

In the continuous mode, furan (ordinarily as a liquid) and an aqueous solution of butynediol, which can be prepared by reacting acetylene and formaldehyde as shown in U.S. Pat. No. 3,650,985 to Kirchner, are separately introduced into a conventional pressure reactor packed with the catalyst, in any convenient butynediol/furan weight ratio, ordinarily 1/99–99/1, preferably 10/90–90/10. The product, a solution of butanediol, THF and water, in the same relative proportions as those in the feedstock, is continually withdrawn from the reactor. The butanediol and THF can then be separated by conventional fractional distillation, and separately refined if this is needed.

A batch operation can be conducted under the same conditions, using the same reactant ratios. A suitable vessel is charged with furan, an aqueous solution of butynediol and 1–20% by weight of catalyst.

The vessel is then pressurized with hydrogen, brought to the desired temperature and shaken. When the reaction is finished, as determined by cessation of hydrogen consumption, the pressure is released, the product is withdrawn and the components separated and refined as before.

INDUSTRIAL APPLICABILITY

The product of the butynediol portion of the process, 1,4-butanediol, is a commodity in the chemical industry, widely used as a reactant in the preparation of polyesters.

The product of the furan portion, THF, is likewise a commodity and is widely used as a solvent and as a starting material in the preparation of polymeric glycols, which in turn are useful in preparing polyurethanes.

EXAMPLES

In the following examples, all parts are by weight.

EXAMPLE 1

Best Mode

Into a fixed-bed column reactor 76 cm long, with an inside diameter of 4.5 cm, were packed 1500 g of Raney nickel alloy 25% of whose aluminum had been removed with caustic.

1,4-butynediol, a 50% aqueous solution prepared as shown in U.S. Pat. No. 3,560,576, was continually fed into the bottom of the column at the rate of 14 ml per minute.

Furan was simultaneously fed into the bottom of the column at the rate of 3 ml per minute.

Hydrogen was pumped into the bottom of the column at a superficial gas velocity of about 30.5 cm/minute and maintained in the column at a pressure of about 27580 kPa (gauge).

The exit temperature of the product was maintained at about 130° C. by recycling.

The product, an aqueous solution of butanediol and THF in the same mole ratio to each other as that of the reactants from which they were prepared, was continuously withdrawn from the top of the column.

EXAMPLE 2

Into a shaker tube were charged
1,4-butynediol (50% solution in water): 80 parts
Furan: 20 parts
Raney nickel (slurry grade, from which substantially all aluminum had been removed): 10 parts The resulting slurry was adjusted to pH 10–11 with a 25% aqueous solution of NaOH. The slurry was then heated to and held at a temperature of 140° C. and under a hydrogen pressure of 27580 kPa (gauge), and shaken for two hours.

The product was a solution, the organic portion of which contained
THF: 28%
Butanediol: 62%

I claim:
1. A process for the simultaneous hydrogenation of 2-butyne-1,4-diol to 1,4-butanediol and furan to tetrahydrofuran, the process comprising
   (a) simultaneously bringing furan and an aqueous solution of 2-butyne-1,4-diol into contact, in a reaction zone, with
      (1) a hydrogenation catalyst, and
      (2) hydrogen under pressure, while maintaining the reaction mass at a temperature of 60°–150° C., and
   (b) withdrawing from the reaction zone a solution of tetrahydrofuran, 1,4-butanediol and water.

2. The process of claim 1 in which the catalyst used is a granular foraminous alloy of 40–45% by weight of nickel and 55–60% by weight of aluminum, and which has been activated by removal of 5–100% of its aluminum.

3. The process of claim 1 in which the reaction mass is maintained at a temperature of 70°–145° C., and the hydrogen is at a partial pressure of 17236–37920 kPa.

4. The process of claim 1 run continuously.

* * * * *